ary 29, 1980

United States Patent [19]

Chatterjee et al.

[11] 4,200,557
[45] Apr. 29, 1980

[54] ABSORBENT PRODUCT INCLUDING GRAFTED INSOLUBILIZED CELLULOSE ETHER

[75] Inventors: Pronoy K. Chatterjee, Spotswood; Robert F. Schwenker, Jr., Belle Mead, both of N.J.

[73] Assignee: Personal Products Company, Milltown, N.J.

[21] Appl. No.: 842,762

[22] Filed: Oct. 17, 1977

Related U.S. Application Data

[60] Division of Ser. No. 682,692, May 3, 1975, abandoned, which is a continuation-in-part of Ser. No. 581,003, May 27, 1975, abandoned, which is a continuation-in-part of Ser. No. 422,627, Dec. 7, 1973, Pat. No. 3,889,678.

[51] Int. Cl.$^2$ .................................................. C08L 1/28
[52] U.S. Cl. .................................. 260/17 A; 128/284; 128/285; 128/290 R
[58] Field of Search .................................... 260/17 A

[56] References Cited

U.S. PATENT DOCUMENTS

| 3,055,369 | 1/1962 | Graham, Jr. ..................... 128/285 |
| 3,067,745 | 12/1962 | Burgeni et al. ..................... 128/285 |
| 3,298,979 | 1/1967 | Hagemeyer et al. ................. 260/17 |
| 3,491,039 | 1/1970 | Takahashi et al. ..................... 260/17 |
| 3,492,082 | 1/1970 | Lee ......................................... 260/17 |
| 3,522,158 | 1/1970 | Garnett et al. ........................... 260/17 |
| 3,589,364 | 6/1971 | Dean et al. ............................. 128/284 |
| 4,028,290 | 6/1977 | Reid ............................... 260/17.4 CL |
| 4,044,766 | 8/1977 | Kaczmarzyk ......................... 128/285 |

OTHER PUBLICATIONS

Chem. Absts. 67:64749s, "Photochemical Grafting of Acrylonitrile on Carboxy Methyl Cellulose," Vasiliu et al.

*Primary Examiner*—Edward M. Woodberry
*Attorney, Agent, or Firm*—Jason Lipow

[57] ABSTRACT

An insoluble etherified cellulose graft copolymer is provided comprising etherified cellulose which is soluble in water in the absence of grafting and is chosen from the group consisting of the alkali metal salts of carboxyalkyl cellulose, sulfoalkyl cellulose and phosphonoalkyl cellulose. The etherified cellulose has grafted onto its cellulose backbone side chains of polymer moieties in sufficient quantities to render the grafted etherified cellulose insoluble. The products of this invention are used alone or mixed with other absorbent materials such as unmodified cellulose, in the manufacture of absorbent napkins, tampons, sponges and the like.

18 Claims, No Drawings

ABSORBENT PRODUCT INCLUDING GRAFTED INSOLUBILIZED CELLULOSE ETHER

This is a division of our copending application Ser. No. 682,692 filed on May 3, 1976, now abandoned, which was a continuation in part of our copending application Ser. No. 581,003 filed on May 27, 1975, now abandoned, which was a continuation in part of our then copending application Ser. No. 422,627 filed on Dec. 7, 1973 and now issued as U.S. Pat. No. 3,889,678, issued June 17, 1975.

BACKGROUND OF THE INVENTION

This invention relates to highly absorbent materials made by chemically modifying the naturally occurring structure of cellulose. Specifically, cellulose is etherified to a sufficiently high degree to produce alkali metal cellulose ethers which are soluble in water and is then modified by grafting to produce highly absorbent insoluble cellulose ether salts.

Cellulose fiber and regenerated cellulose are raw materials for many commercial absorbent products including, for example, such products for absorbing body fluids as catamenial napkins and tampons, diapers and surgical dressings. While, in the main, unmodified cellulose has proven useful in such products, in an effort to improve product quality and economy, the art has searched for improved materials. It was discovered, for example, that alkali metal salts of cellulose ethers such as sodium carboxymethyl cellulose exhibited increased absorption and retention properties for body fluids, these desirable properties increasing with the degree of ether substitution (D.S.). Accordingly, such materials in, of course, insoluble form are useful in products for absorbing body fluids, such teachings being disclosed in U.S. Pat. No. 3,005,456, issued to Graham on Oct. 24, 1961. Further in U.S. Pat. No. 3,589,364 issued to W. L. Dean and G. N. Ferguson on June 29, 1971, there is disclosed a particular form of insoluble, sodium carboxymethyl cellulose having a high degree of substitution of ether groups and insolubilized by wet crosslinking the cellulose using methods such as are described in U.S. Pat. No. 3,241,553, issued to F. H. Steiger on Mar. 22, 1966. In U.S. Pat. No. 3,678,031, still another form of insoluble carboxymethyl cellulose is disclosed having a high degree of substitution, and in this case, insolubilized by an acid and heat treatment. U.S. Pat. No. 3,256,372 to Adams et al. discloses grafting hydrophilic polymers to the cellulose backbone and, in our application Ser. No. 422,627, now U.S. Pat. No. 3,889,678, we disclose still another chemical modification of cellulose whereby a balanced quantity of ionic and nonionic copolymer moieties are grafted to the cellulose backbone and may be grafted to modified forms of cellulose as well.

Each of these references teach modified forms of cellulose which represent great improvements in absorption and retention capacities for body fluids over the properties of unmodified cellulose. Notwithstanding these prior art improvements, the search continues for still better absorbents.

SUMMARY OF THE INVENTION

It has now been discovered that a form of modified cellulose may be provided which far exceeds the absorption and retention properties of prior art modified cellulose and hence, is advantageously employed as an absorption media in an absorbent body for products such as catamenial napkins and tampons, diapers and dressings provided for absorbing and retaining body fluids. In accordance with this invention, an insoluble etherified cellulose graft copolymer is provided comprising an alkali metal salt of an etherified cellulose which is soluble in water in the absence of grafting and is insolubilized by having, grafted to the cellulose backbone, a quantity of side chains of polymer moieties sufficient to render said salts of said ethers insoluble while still maintaining a high capacity to absorb fluids.

The particular etherified cellulose may be selected from the group consisting of alkali metal salts of carboxyalkyl cellulose, phosphonoalkyl cellulose, sulfoalkyl cellulose and a sufficient quantity of such etherifying groups are present per anhydroglucose unit in the cellulose chain to render such salts water-soluble if the grafted polymer groups were not present. Such a degree of ether substitution (D.S.) of at least 0.35 ether groups per anhydroglucose unit is generally sufficient. Such alkali metal salts are, for example, the Li, Na, K, or Cs salts.

The salts of the cellulose ethers are rendered insoluble by grafting, to the cellulose backbone, side chains of homopolymer or copolymer moieties which side chains may be made up of hydrophilic, hydrophobic or both hydrophilic and hydrophobic polymeric moieties and should be present in sufficient quantities to render the salts water-insoluble. The quantity of side chains which must be grafted to the backbone will vary in accordance with the type of substituted group and the D.S. of the ungrafted cellulose ether salt. For example, in the case of alkali metal carboxymethyl cellulose at a D.S. of 0.4, the side chains should constitute approximately at least 10% by weight of the grafted cellulose ether salt. At a D.S. of 1.2, the side chains should be at least about 25% by weight of the grafted cellulose ether salt. The side chains could constitute as much as 90% or more.

While polymers that are hydrophilic and polymers that are hydrophobic or copolymers being both hydrophilic and hydrophobic may be grafted to the cellulose backbone, particular advantage accrues in using either the hydrophilic polymer or the hydrophilic/hydrophobic copolymers as with these, the resulting grafted cellulose ether salt exhibits even greater absorption and retention properties, this surprisingly being the case without sacrificing insolubility.

DETAILED DESCRIPTION OF THE INVENTION

In accordance with this invention, a product is provided which is the result of having cellulose undergo the two chemical reactions of etherification and polymer grafting. The starting material for these reactions may be natural cellulose fibers such as, for example, wood pulp, hemp, bagasse, cotton, and the like or may be a regenerated cellulose fiber such as rayon.

Preferably, the etherified cellulose is selected from the group consisting of the alkali metal salts of carboxyalkyl cellulose, phosphonoalkyl cellulose or sulfoakly cellulose.

Etherification is generally accomplished by reacting cellulose with an etherification reagent in an alkaline dispersing media. For example, sodium carboxymethyl cellulose may be made by the process described by R. L. Whisler in "Carbohydrate Chemistry", Vol. III (Cellulose), at pages 322-327, Academic Press, Inc. (1963) wherein there is disclosed methods of converting cellulosic materials, notably cotton linters, into carboxymethyl cellulose by reaction with chloracetic acid and aqueous sodium hydroxide in a propanol solution. The so-called slurry processes for manufacturing sodium carboxymethyl cellulose is described in U.S. Pat. No. 3,347,855 issued to Russel Nelson on Oct. 17, 1967 wherein the degree of etherification (D.S.) is controlled and can be varied in the range of from about 0.4 to about 1.6. This product is available commercially in either powdered or fibrous form, although it should be noted that even higher D.S. products ranging from 2.5–2.77 can be made in accordance with the process described in the aforementioned publication by Whistler.

Phosphonoalkyl cellulose may be made in a similar manner employing a phosphonoalkylating reagent solution comprising a basic aqueous solution of a compound of the structure:

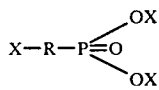

wherein X is a halogen and R is an alkylene radical. A preferred reagent is chloromethylphosphonic dichloride.

Sulfoalkyl cellulose may be made in a similar manner employing sulfoalkylating reagent solution comprising a basic aqueous solution of a compound of the structure:

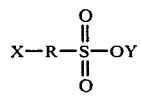

wherein X is a halogen, R is an alkylene radical and Y is chosen from the group consisting of a halogen, hydrogen, or alkali metal atom. A preferred reagent is chloroethylsulfonic acid.

The resulting salt of cellulose ether should have sufficient etherifying groups to render it water-soluble in the absence of other treatment. Generally, for an alkali metal salt of carboxymethyl cellulose ether, a D.S. of at least about 0.35 will accomplish this result. As is well-known in the art, the D.S. may be controlled during the etherification process by controlling the reaction time and temperature and the proportions of reactants.

In accordance with this invention, the salts of those ethers have grafted onto the cellulose backbone thereof, side chains of polymer or copolymer moieties in sufficient quantity to render the grafted product insoluble in water. Such side chains may comprise hydrophilic or hydrophobic moieties and, in fact, a given molecule of cellulose ether salt could be provided with various combinations of these kinds of polymers.

Hydrophilic polymer moieties usable for this purpose may be, for example, poly(acrylic acid), sodium poly(acrylate), poly(methacrylic acid), potassium poly(methacrylate), poly(vinyl alcohol sulfate), poly(phosphoric acid), poly(vinyl amine), poly(4-vinyl pyridine), hydrolyzed poly (acrylonitrile) and the like.

Also usable are hydrophobic polymers such as, for example, poly(methyl methacrylate), poly(ethyl methacrylate), poly(ethyl acrylate), poly(butyl acrylate), poly(vinyl acetate), poly(styrene), poly(butadiene), poly(isoprene), and the like.

Copolymers of any of these groups are likewise usable and, in particular, still greater enhancement of absorption and retention properties are realized when at least a portion of the polymer moieties are chosen from the group characterized as hydrophilic.

The cellulose ether salts may be combined with the preformed homo- or copolymers in the first instance, or with the precurser monomers of these polymers with polymerization taking place in situ. In either event, the reactants may be dispersed, and the reaction carried out, in a vapor medium or a non-aqueous medium such as, for example, acetone alcohols (e.g., methanol, ethanol, isopropanol, etc.), benzene, liquid ammonia and the like. Preferably, however, the grafting reaction is carried out in an aqueous medium.

When the grafting is carried out in a liquid medium, to promote dispersion and hence, more uniform polymerization of some monomers (e.g. butadiene), it is desirable to add a few drops of an emulsifier to the reaction mixture. Examples of such an emulsifier are Triton X-100 (one of a class of acrylalkyl polyether alcohols, sulfonates, and sulfates sold by Rohm & Haas); sodium lauryl sulfate; lauryl bromethyl ammonium chloride; a cationic quaternary ammonium salt of the alkyl trimethylammonium chloride and dialkyl dimethylammonium chloride type wherein the average alkyl composition is 90% dodecyl, 9% tetradecyl and 19% oxtadecyl and which is supplied as a solution of 33% active ingredient, 17% sodium chloride, and 50% water by Armour & Co. as Arquad 12; lauryl pyridinium chloride, and the like.

The grafting reaction may be initiated with an ionic initiator (e.g., alkali hydroxides), a cationic initiator (e.g. a Lewis acid such as boron trifluoride), or even with radiation (ultraviolet, gramma, or electron beam radiation). It is preferred, however, that the grafting be carried out by the free radical polymerization mechanism using a free radical initiator such as, for example, ceric ion, ferrous ion, cobaltic ion, $(NH_4)_2S_2O_8$ cuprous ion, and the like. The ceric ion initiator is preferred.

Because most free radical reactions are inhibited by the presence of oxygen, it is desirable to flush out essentially all the oxygen from the reaction vessels by bubbling an inert non-oxidizing gas such as nitrogen, helium, argon, etc., through the system prior to the addition of the free radical initiator.

The pH range used for the reaction depends on the particular initiator used. One could use anywhere from a highly acidic pH (0.8–2.3) to a highly basic pH (12–14), depending on the choice of initiator. For the preferred ceric ion initiator, the pH should be acidic, i.e., less than seven and preferably about 0.8 to about 2.3.

The grafting reaction may be carried out at temperatures ranging from room temperature (i.e. 20° to 30° C.) to the normal boiling point of the lowest boiling component of the mixture. If the reaction is carried out under greater than atmospheric pressure, the temperature could then be raised above the normal boiling point of the lowest boiling component of the mixture. The reaction mixture may also be cooled below room temperature, if desired.

A satisfactory product may be obtained by grafting either inherently hydrophilic or hydrophobic polymers or mixed copolymers to the cellulose in the manner described above. However, as is pointed out herein, particular advantage accrues to ethers grafted with at least partially hydrophilic chains and a satisfactory method of accomplishing this is to first graft, by the method described above, a polymer which is at least partially hydrolyzable and then subsequently hydrolyzing the product to produce an at least partially hydrophilic grafted chain. Such hydrolyzable polymer is for example, polyacrylonitrile which can be hydrolyzed to hydrophilic alkali metal poly(acrylate). When copolymers of polyacrylonitrile and relatively non-hydrolyzable polymer moieties, e.g. methyl methacrylate, ethyl acrylate, butadiene and the like, are grafted to the cellulose ether and subsequently hydrolyzed in a controlled manner, a mixed polymer chain results which is partially hydrophilic and partially hydrophobic. Hydrolyzation is accomplished by reacting the grafted ethers, preferably under reflux, with an excess of a solution of a strong base, e.g., sodium hydroxide, potassium hydroxide, lithium hydroxide, and like bases. The concentration of this solution may be from about 1% to about 50% by weight.

The weight percent of polymer grafted to the cellulose ether (based on the weight of grafted ether) depends to the major extent upon the D.S. of the ether. Generally, the greater the D.S., the greater the weight percent of grafted polymer required to render the otherwise water-soluble cellulose ether insoluble. It has been found that this relationship is essentially independent of the nature of the polymer, i.e., the hydrophilicity or hydrophobicity of the polymer.

The following table illustrates this relationship using sodium carboxymethyl cellulose of varying D.S. as exemplary cellulose ethers.

| MINIMUM POLYMER GRAFTING TO INSOLUBILIIZE SODIUM CARBOXYMETHYL CELLULOSE | | | | | | | | | | | |
|---|---|---|---|---|---|---|---|---|---|---|---|
| Degree of Substitution of CMC | 0.3 | 0.4 | 0.5 | 0.6 | 0.7 | 0.8 | 0.9 | 1.0 | 1.1 | 1.2 | 1.3 |
| Minimum Polymer Add-On (%) | 0 | 9 | 12 | 13 | 14 | 15 | 17 | 19 | 21 | 23 | 27 |

The grafted cellulose ether salts of this invention have been found to be significantly greater in both absorption and retention properties over prior chemically modified forms of cellulose and even over the grafted unetherified cellulose described in our above referenced U.S. Pat. No. 3,889,678. While the products of this invention may be used in the form of powders, it is preferred that, when they are used in a fibrous absorbent body in a product for absorbing body fluids, they retain the original fibrous structure. Several methods of producing such a fibrous product will occur to one skilled in the art in view of the teachings herein. For example, when the products of this invention are formed by first producing water-soluble alkali metal cellulose ethers and then grafting in an aqueous media, the ungrafted intermediate product can be temporarily water-insolubilized by treating it with an acid solution. Thereafter, the grafting can take place in a water media, while still preserving the fibrous structure. Subsequent to grafting, the product can be treated with an alkali metal hydroxide to convert the ether back to its original alkali metal salt form. Alternatively, the sequence of reaction steps could be varied to either first graft unetherified cellulose and then subsequently etherify or to both graft and etherify essentially simultaneously. In any event, the fibrous structure of the cellulose can be maintained.

The products of this invention may be used alone or mixed with unmodified cellulose, or other absorbent material, in the manufacture of absorbent napkins, tampons, sponges and the like. Fibrous products of this invention either alone or in combination with other materials such as, for example, untreated cellulose, may also be made into nonwoven fabrics or tissue, which fabrics or tissue are useful in the manufacture of absorbent napkins, tampons, sponges and the like.

The grafted cellulose ethers salts of this invention their properties and the methods of preparation will be more fully understood from a consideration of the following examples which are given for the purposes of illustration and are not to be construed as limiting the invention in spirit or in scope except as set forth in the appended claims.

EXAMPLE 1

A series of samples of commercially available sodium carboxymethyl cellulose powder having a D.S. of 0.4–1.2 are obtained from Hercules, Inc. of Wilmington, Delaware. Twenty grams of each sample is converted to the acid form by treating with 250 ml. of a methanol-nitric acid solution (100 ml. $HNO_3$ in one liter MeOH) for twenty-four hours at 25° C. The resulting acidified material is washed thoroughly with distilled water and then placed in a reactor with 1000 ml. of distilled water. Oxygen is removed from the system by purging with nitrogen for one half hour. Ten ml. of a ceric ammonium nitrate solution (0.1 Molar Ce (IV) in 1 Normal nitric acid) was then added and, after five minutes, a predetermined quantity of acrylonitrile (varying from 5 to 30 ml.) is added. The reaction is allowed to proceed for two hours, at 25° C., under a nitrogen atmosphere. The resulting grafted cellulose ethers are transferred to a Buchner funnel and washed thoroughly with water and acetone. The washed ethers are then converted to the alkali metal salt form by being treated with a 5% solution by weight of potassium hydroxide in methanol for 24 hours at 25° C. The product is washed with methanol and dried at 105° C.

The resulting series of hydrophobic-polymer grafted alkali metal cellulose ethers are tested to determine the weight percent of grafted polymer and the water and salt solution absorption and retention properties. The polymer concentration of these samples is determined by nitrogen analysis wherein the nitrogen content of the grafted ethers is obtained by the Kjeldahl method, using an ammonia electrode, this method being described in Official Methods and Analysis of the Association of Official Analytical Chemists, Washington, D.C., 12th Edition, Edited by W. Horowitz, 1975, code no. 47.023.

Aqueous liquid absorbency is determined by the "XOW Test", wherein an approximately one-half gram sample of the test material is accurately weighed and stirred into a beaker containing 100 ml. of the aqueous test fluid. After twenty minutes, the mixture is filtered through a piece of nylon trico fabric and allowed to drain for five minutes. The filtrate is collected and measured in the graduated cylinder. The "XOW", the absorption capacity of the material expressed in units of grams of absorbed liquid per gram of test material is calculated as follows:

$$XOW = \frac{100 - \text{filtrate (ml.)}}{\text{weight of test material (dry)}}$$

Aqueous fluid retention capacity is determined by using a Porous Plate Testing Apparatus, as described in detail in Textile Res. J., 37, pp 356–366, 1967. Briefly, this test involves placing the test material in what is essentially a Buchner funnel having a porous bottom plate and holding the sample in place by applying thereon a standard weight to maintain a standardized confining pressure. The porous plate is placed in contact with a reservoir of liquid and the sample is allowed to absorb liquid through the porous plate until saturated. By maintaining the sample at essentially the level of the reservoir, the liquid absorbed is subjected to essentially a zero hydraulic head with respect to the reservoir. To determine liquid retention, the saturated sample is elevated with respect to the liquid reservoir thereby imposing a hydraulic head upon the liquid absorbed, the head arbitrarily chosen as 35.5 cm. of fluid. The apparatus is provided with means for directly measuring the volume of liquid retained under this hydraulic head. Retention values are reported as the volume retained per unit weight of the sample.

The results of these tests are tabulated in Table I using variously, aqueous salt solutions and water. As a control, ethers, as commercially obtained, are likewise tested and reported as "unmodified". As a further control, ether salts which are acidified following the above-described procedure and then converted back to the salt form without undergoing the grafting reaction are tested and also reported in Table I as, "treated controls". For comparative purposes, wood pulp fibers are also tested and reported as "cellulose fiber".

Table I

ABSORBENCY OF HYDROPHOBIC POLYMER (PAN)[1] GRAFTED CMC (K-SALT) POWDER

| Carboxymethyl Cellulose Powder DS | Polymer Add-On (%) | 1% NaCl Solution Retention (cc/g) Porous Plate | 1.5% NaCl Solution XOW (g/g) | Water XOW (g/g) |
|---|---|---|---|---|
| 0.4 (unmodified) | 0 | NA | NA[2] | NA |
| 0.4 (treated control) | 0 | NA | NA | NA |
| 0.4 | 3.9 | NA | NA | NA |
| 0.4 | 17.2 | 8.1 | 22 | 56 |
| 0.4 | 37.9 | 4.6 | 10 | 11 |
| 0.4 | 38.2 | 4.4 | 16 | 18 |
| 0.7 (unmodified) | 0 | NA | NA | NA |
| 0.7 | 0 | NA | NA | NA |

Table I-continued

ABSORBENCY OF HYDROPHOBIC POLYMER (PAN)[1] GRAFTED CMC (K-SALT) POWDER

| Carboxymethyl Cellulose Powder DS | Polymer Add-On (%) | 1% NaCl Solution Retention (cc/g) Porous Plate | 1.5% NaCl Solution XOW (g/g) | Water XOW (g/g) |
|---|---|---|---|---|
| (treated control) 0.7 | 3.7 | NA | NA | NA |
| 0.7 | 13.4 | 6.5 | 22 | 60 |
| 0.7 | 19.5 | 5.6 | 18 | 34 |
| 0.7 | 41.9 | 3.4 | 10 | 11 |
| 0.9 (unmodified) | 0 | NA | NA | NA |
| 0.9 (treated control) | 0 | NA | NA | NA |
| 0.9 | 12.7 | NA | NA | NA |
| 0.9 | 25.5 | 5.8 | 18 | 18 |
| 0.9 | 34.6 | 3.8 | 14 | 19 |
| 1.2 (unmodified) | 0 | NA | NA | NA |
| 1.2 (treated control) | 0 | NA | NA | NA |
| 1.2 | 0.7 | NA | NA | NA |
| 1.2 | 15.0 | NA | NA | NA |
| 1.2 | 27.4 | 3.3 | 12 | 20 |
| 1.2 | 41.4 | 2.3 | 9 | 12 |
| Cellulose Fiber (reference) | — | 1.5 | 16 | 16 |

[2]NA - Not applicable because the material was soluble or gelled in fluid.
[1]PAN - Polyacrylonitrile As can be seen from the results of Table I, the grafting technique of this invention has insolubilized the etherified cellulose and has generally endowed the resulting product with absorbency properties (XOW values) at least as good as those of wood pulp. The retention values have increased markedly.

EXAMPLE 2

The procedure of Example 1 is carried out with the exception that the grafted polymer is rendered hydrophilic by undergoing a hydrolysis step to convert the polyacrylonitrile to alkali metal polyacrylate. The acidified grafted cellulose ethers resulting from the grafting step of Example 1 are hydrolyzed by being refluxed with a solution of 6% potassium (or where noted, sodium) hydroxide in a solution of 90% ethanol/20% water, by volume, for one hour and then washed with an ethanol/water solution and dried at 105° C. Polymer content and absorption and retention properties are determined by the method described in Example I and the results are reported in Table II.

Table II

ABSORBENCY OF HYDROPHILIC POLYMER (ALKALI METAL-POLYACRYLATE) GRAFTED CMC (ALKALI METAL-SALT) POWDER

| Carboxymethyl Cellulose Powder DS | Polymer Add-On (%) | Alkali Metal | 1% NaCl Solution Retention (cc/g) Porous Plate | 1.5% NaCl Solution XOW (g/g) | Water XOW (g/g) |
|---|---|---|---|---|---|
| 0.4 (unmodified) | 0 | K | NA[1] | NA | NA |
| 0.4 (treated control) | 0 | K | NA | NA | NA |
| 0.4 | 3.9 | K | NA | NA | NA |
| 0.4 | 17.2 | K | 9.1 | 32 | 114 |
| 0.4 | 23.1 | Na | 10.0 | 24 |  |
| 0.4 | 37.9 |  | 13.8 | 30 | 126 |
| 0.4 | 38.2 |  | 10.5 | 29 | 119 |
| 0.4 | 56.5 | Na | 16.5 | 33 |  |
| 0.4 | 79.6 | Na | 23.8 | 46 |  |

Table II-continued
ABSORBENCY OF HYDROPHILIC POLYMER (ALKALI METAL-POLYACRYLATE) GRAFTED CMC (ALKALI METAL-SALT) POWDER

| Carboxymethyl Cellulose Powder DS | Polymer Add-On (%) | Alkali Metal | 1% NaCl Solution Retention (cc/g) Porous Plate | 1.5% NaCl Solution XOW (g/g) | Water XOW (g/g) |
|---|---|---|---|---|---|
| 0.4 | 89.9 | Na | 26.3 | 46 | |
| 0 (unmodified) | 0 | | NA | NA | NA |
| 0 (treated control) | 0 | | NA | NA | NA |
| 0.7 | 3.7 | K | NA | NA | NA |
| 0.7 | 13.4 | K | 4.8 | 40 | 98 |
| 0.7 | 19.5 | K | 5.9 | 43 | 106 |
| 0.7 | 41.9 | K | 5.3 | 46 | 126 |
| 0.7 | 44.1 | K | — | 41 | Na |
| 0.7 | 48.2 | K | 25.0 | 44 | Na |
| 0.7 | 71.0 | K | 19.3 | 46 | Na |
| 0.7 | 82.9 | K | 24.4 | 49 | Na |
| 0.7 | 91.5 | K | 22.6 | 47 | Na |
| 0.9 (unmodified) | 0 | K | NA | NA | NA |
| 0.9 (treated control) | 0 | K | NA | NA | NA |
| 0.9 | 12.7 | K | NA | NA | NA |
| 0.9 | 25.5 | K | 10.0 | 42 | 117 |
| 0.9 | 34.4 | K | 8.5 | 44 | 100 |
| 0.9 | 75.5 | K | 18.6 | 42 | Na |
| 1.2 (unmodified) | 0 | K | NA | NA | NA |
| 1.2 (treated control) | 0 | K | NA | NA | NA |
| 1.2 | 0.7 | K | NA | NA | NA |
| 1.2 | 15.0 | K | NA | NA | NA |
| 1.2 | 27.4 | K | 4.9 | 43 | 82 |
| 1.2 | 41.4 | K | 7.3 | 42 | 93 |
| 1.2 | 77.1 | K | 23.7 | 45 | NA |
| Cellulose Fiber (reference) | — | | 1.5 | 16 | 16 |

[1]NA - Not applicable because the material was soluble in fluid.

As in the prior example, it can be seen from Table II that soluble cellulose ether salts have been successfully insolubilized by grafting. Notwithstanding this insolubilization, it should be noted that in this case of grafted hydrophilic polymer moieties, the XOW values of the grafted ether salts far exceed that of cellulose fibers. As in the foregoing example, retention values are also greatly improved.

EXAMPLE 3

The procedure of Example 2 is carried out with the exception that, in addition to adding acrylonitrile to the grafting reactor, various quantities of ethyl acrylate are added so as to graft, to the cellulose, polymer moieties of both poly(ethyl acrylate) and poly(acrylonitrile). These grafted copolymer ether salts are then hydrolyzed in accordance with the method set out in Example 2, to produce an at least partially hydrophilic polymer moiety grafted to the cellulose backbone. The quantity of polymer add-on is determined by measuring the differential weight before and after grafting. Additionally, the retention and absorbency of these grafted copolymer ethers is measured and reported in Table III.

Table III
ABSORBENCY OF HYDROLYZED COPOLYMER GRAFTED CMC POWDER (Na SALT)[1]

| Carboxymethyl Cellulose DS | Monomer Ratio in Grafted CMC | Copolymer Add-On (%) | XOW (g/g) in 1.5% NaCl Solution |
|---|---|---|---|
| 0.4 (unmodified) | — | 0 | NA |
| 0.4 (treated control) | — | 0 | NA |
| 0.4 | 1:1 AN[3]/EA[4] (hydrolyzed) | 82.5 | 48 |
| 0.4 | 3:1 AN/EA (hydrolyzed) | 84.4 | 34 |
| 0.4 | 3:1 AN/EA (hydrolyzed) | 84.4 | 64[2] |
| 0.7 (unmodified) | — | 0 | NA |
| 0.7 (treated control) | — | 0 | NA |
| 0.7 | 1:1 AN/EA (hydrolyzed) | 74.9 | 51 |
| 0.7 | 3:1 AN/EA (hydrolyzed) | 79.1 | 35 |
| 0.9 | — | 0 | NA |

Table III-continued

ABSORBENCY OF HYDROLYZED COPOLYMER GRAFTED CMC POWDER (Na SALT)[1]

| Carboxymethyl Cellulose DS | Monomer Ratio in Grafted CMC | Copolymer Add-On (%) | XOW (g/g) in 1.5% NaCl Solution |
|---|---|---|---|
| (unmodified) 0.9 | — | 0 | NA |
| (treated control) 0.9 | 1:1 AN/EA (hydrolyzed) | 68.3 | 52 |
| 0.9 | 3:1 AN/EA (hydrolyzed) | 71.3 | 34 |
| 1.2 (unmodified) | — | 0 | |
| 1.2 (treated control) | — | 0 | |
| 1.2 | 1:1 (hydrolyzed) | 74.2 | 60[2] |
| 1.2 | 3:1 (hydrolyzed) | 76.1 | 37 |
| Cellulose Fiber (reference) | — | — | 16 |

[1] Hydrolyzed cellulose poly(ethyl acrylate-acrylonitrile) copolymer
[2] Tendency to Gel
[3] AN - acrylonitrile
[4] EA - Ethyl acrylate
NA - Not applicable because the material was soluble in fluid.

As can be seen from the table, the copolymer grafting has resulted in insolubilizing the otherwise soluble cellulose ethers. The XOW values show that the copolymer graft results in a product more absorbent than wood pulp or the hydrophobic homopolymer graft and somewhat less absorbent than the hydrophilic homopolymer graft.

EXAMPLE 4

A series of fibrous sodium carboxymethyl cellulose are prepared in accordance with the method described in Methods of Carbohydrate Chemistry, Vol. III, Edit R. L. Whistler, Academic Press, N.Y. (1963), p. 322, whereby fifteen grams of southern pine, kraft, fully bleached, wood pulp is slurried into 400 mls. of isopropanol. Forty mls. of 23% by weight aqueous sodium hydroxide are slowly stirred into this slurry for a period of 30 minutes at room temperature. Eighteen grams of monochloroacetic acid are slowly added, by stirring into the mixture for a period of 30 minutes and the mixture is allowed to react for a period of 3½ hours while being maintained at a temperature of 55° C. The so-treated fibers are then filtered from the reaction mixture and transferred to a beaker containing a mixture of 70%/30% by volume, methanol-water solution and sufficient acetic acid is added to neutralize the so-formed slurry. The slurry is filtered and the resulting fibers are washed; first with a 70%/30% by volume methanol-water wash and then with a 95%/5% by volume, methanol-water wash. The washed fibers are dried at 70° C. for two hours. The resulting product is fibrous sodium carboxymethyl cellulose having a degree of substitution of 0.64. Various quantities, as reported in Table IV below, of hydrolyzed acrylonitrile homopolymer and acrylonitrile/ethyl acrylate copolymer are grafted to the fibrous cellulose ethers following the procedures of the foregoing examples 2 and 3. The XOW values for these grafted samples as well as treated and untreated controls and a comparative unetherified cellulose fiber sample, are likewise reported in Table IV.

Table IV

ABSORBENCY OF HYDROPHILIC POLYMER GRAFTED TO Na CMC FIBER AND HYDROLYZED COPOLYMER GRAFTED TO Na CMC FIBER

| Carboxymethyl Cellulose DS | Monomer Ratio in Grafted CMC | Total Polymer Add-On (%) | XOW (g/g) in 1.5% NaCl Solution |
|---|---|---|---|
| 0.64 (Na-Salt) | — | 0 | Soluble |
| 0.64 (treated control K-Salt) | — | 0 | Soluble |
| Na 0.64 | AN (hydrolyzed) | 74.8 | 51 |
| Na 0.64 | AN (hydrolyzed) | 88.6 | 82* |
| Na 0.64 | AN (hydrolyzed) | 88.6 | 46 |
| Na 0.64 | AN (hydrolyzed) | 88.6 | 45 |
| Na 0.64 | 3:1 AN/EA (hydrolyzed) | 83.9 | 40 |
| Na 0.64 | 1:1 AN/EA (hydrolyzed) | 69.9 | 48 |
| Na 0.64 | 1:1 AN/EA (hydrolyzed) | 82.9 | 49 |
| Na 0.64 | 1:1 AN/EA (hydrolyzed) | 87.8 | 40 |
| Na 0.64 | 1:3 AN/EA (hydrolyzed) | 81.3 | 59 |
| Na 0.64 | EA (hydrolyzed) | 83.6 | 100* |
| Cellulose Fiber (reference) | — | 0 | 16 |

*Tendency to form gel

COMPARATIVE EXAMPLE

For comparative purposes, unmodified and several chemically modified cellulosic materials are evaluated for their fluid retention and XOW values and tabulated in Table V which follows. The material designated as "Cellulose Fibers" is untreated, comminuted, southern pine, kraft, fully bleached wood pulp. The material designated "CMC" is sodium carboxymethyl cellulose powder having a D.S. of 0.35 or greater and obtained from Hercules, Inc. The material designated as "Crosslinked CMC" is wet crosslinked sodium carboxymethyl cellulose made in accordance with the methods described in the aforementioned U.S. Pat. No. 3,589,364 issued to Dean, et al. The material designated as "Hydrolyzed PAN Grafted Cellulose" is a natural, unetherified cellulose having grafted thereto a completely hydrophilic hydrolyzed poly(acrylonitrile) homopolymer, said polymer constituting approximately 66% by weight of the grafted fiber. The material designated as "Hydrolyzed Copolymer Grafted Cellulose" is an unetherified cellulose having grafted thereon a partially hydrolyzed acrylonitrile/ethyl acrylate copolymer in a 50/50 molar monomer ratio, said copolymer representing approximately 90% by weight of the grafted cellulose and being the material described and claimed in our aforementioned co-pending application U.S. Ser. No. 422,627. These materials are compared, for their fluid retention and XOW values, to samples of the etherified grafted cellulose of this invention, also tabulated below and referenced to tables herein.

Table V

COMPARISON OF ABSORPTION CAPABILITIES OF DIFFERENT ABSORBENT FIBERS AND SELECTED POLYMER GRAFTED Na CMC SAMPLES

| Materials | Material Description References | Fluid Retention (cc/g) 1% NaCl Solution | XOW (g/g) in 1.5% NaCl Solution |
|---|---|---|---|
| Cellulose Fibers | — | 1.5 | 16 |
| CMC (DS>0.35) | — | Dissolved | Dissolved |
| Crosslinked CMC (DS ≃ 0.7) | — | 10 | 22–24 |
| Hydrolyzed PAN Grafted Cellulose | — | 14 | 27–28 |
| Hydrolyzed Copolymer Grafted Cellulose | — | 11 | 22–26 |
| Polymer Grafted CMC | | | |
| 0.4 DS/56.5% Polymer | See Table II | 17 | 33 |
| 0.4 DS/79.6% Polymer | " | 24 | 46 |
| 0.4 DS/89.9% Polymer | " | 26 | 46 |
| 0.7 DS/48.2% Polymer | " | 25 | 44 |
| 0.7 DS/71.0% Polymer | " | 19 | 46 |
| 0.7 DS/82.9% Polymer | " | 24 | 49 |
| 0.9 DS/75.5% Polymer | " | 19 | 42 |
| 1.2 DS/77.1% Polymer | " | 24 | 45 |
| 0.4 DS/84.4% Copolymer | See Table III | — | 64 |
| 0.7 DS/74.9% Copolymer | " | — | 51 |
| 0.9 DS/68.3% Copolymer | " | — | 52 |

As Table V shows, in all cases, the materials of this invention exceeded, both in fluid retention and in XOW values, each of the samples of the various other chemically modified and unmodified cellulosics to which they were compared.

What is claimed is:

1. An improvement in an absorbent product for absorbing body fluids comprising water-insoluble, cellulose ether selected from the group consisting of carboxyalkyl cellulose, sulfoalkyl cellulose and phosphonoalkyl cellulose; said ether having a degree of substitution ranging from about 0.4 to about 1.3 average number of ether groups per anhydroglucose unit; the improvement comprising said ether having grafted onto its cellulose backbone side chains of hydrophilic polymer moieties in an amount which ranges from about 10 to about 90% by weight, based on the weight of the grafted cellulose ether and sufficient to render said grafted cellulose ether insoluble and to provide said grafted cellulose ether with an XOW in 1.5% by weight aqueous sodium chloride solution of at least 30.

2. The absorbent product of claim 1 wherein the hydrophilic polymer moieties are selected from the group consisting of poly(acrylic acid), sodium poly(acrylate), poly(methacrylic acid), potassium poly(methacrylate), poly(vinyl alcohol sulfate), poly(phosphoric acid), poly(vinyl amine), poly(4-vinyl pyridine), and hydrolyzed poly(acrylonitrile).

3. The absorbent product of claim 2 wherein the hydrophilic polymer moiety comprises hydrolyzed poly(acrylonitrile).

4. The absorbent product of claim 1 wherein said chains of polymer moieties are copolymers of hydrophilic and hydrophobic polymer moieties.

5. The absorbent product of claim 4 wherein said hydrophobic polymer moieties comprise polymer moieties selected from the group consisting of poly(methyl methacrylate), poly(ethyl methacrylate), poly(ethyl acrylate), poly(butyl acrylate), poly(vinyl acetate), poly(styrene), poly(butadiene), and poly(isoprene).

6. The absorbent product of claim 1 which is a sanitary napkin.

7. The absorbent product of claim 1 which is a catamenial tampon.

8. The absorbent product of claim 1 which is a diaper.

9. An improvement in an absorbent product for absorbing body fluids comprising water-insoluble carboxyalkyl cellulose having a degree of substitution ranging from about 0.4 to about 1.3 average number of carboxyalkyl groups per anhydroglucose unit; the improvement comprising said carboxyalkyl cellulose having grafted unto its cellulos backbone side chains of hydrophilic polymer moieties in an amount which ranges from about 10° to about 90° by weight, based on the weight of the grafted carboxyalkyl cellulose and sufficient to render said grafted carboxyalkyl cellulose insoluble and to provide said grafted carboxyalkyl cellulose with an XOW in 1.5% by weight aqueous sodium chloride solution of at least 30.

10. The absorbent product of claim 9 wherein the hydrophilic polymer moieties are selected from the group consisting of poly(acrylic acid), sodium poly(acrylate), poly(methacrylic acid), potassium poly(methacrylate), poly(vinyl alcohol sulfate), poly(phosphoric acid), poly(vinyl amine), poly(4-vinyl pyridine) and hydrolyzed poly(acrylonitrile).

11. The absorbent product of claim 10 wherein the hydrophilic polymer moiety comprises hydrolyzed poly(acrylonitrile).

12. The absorbent product of claim 9 wherein said carboxyalkyl cellulose comprises carboxymethyl cellulose.

13. The absorbent product of claim 12 wherein said polymer moieties are present in at least the quantities defined by the relationship:

| Degree of Substitution of Carboxymethyl Cellulose | 0.3 | 0.4 | 0.5 | 0.6 | 0.7 | 0.8 | 0.9 | 1.0 | 1.1 | 1.2 | 1.3 |
|---|---|---|---|---|---|---|---|---|---|---|---|
| Minimum Polymer (% by weight based on weight of said grafted carboxymethyl cellulose) | 0 | 9 | 12 | 13 | 14 | 15 | 17 | 19 | 21 | 23 | 27 |

14. The absorbent product of claim 9 wherein said chains of polymer moieties are copolymers of hydrophilic and hydrophobic polymer moieties.

15. The absorbent product of claim 14 wherein said hydrophobic polymer moieties comprise polymer moieties selected from the group consisting of poly(methyl methacrylate), poly (ethyl methacrylate), poly(ethyl acrylate), poly(butyl acrylate), poly(vinyl acetate), poly(styrene), poly(butadiene), and poly(isoprene).

16. The absorbent product of claim 9 which is a sanitary napkin.

17. The absorbent product of claim 9 which is a catamenial tampon.

18. The absorbent product of claim 9 which is a diaper.

* * * * *